United States Patent [19]

Boschelli et al.

[11] Patent Number: 5,571,825

[45] Date of Patent: Nov. 5, 1996

[54] METHOD OF SELECTIVELY INHIBITING PROSTAGLANDIN G/H SYNTHASE-2

[75] Inventors: Diane H. Boschelli, Plymouth; David T. Connor; Richard D. Dyer, both of Ann Arbor; Sonya S. Khatana, Northville, all of Mich.; James B. Kramer, Sylvania, Ohio; William H. Roark, Ann Arbor, Mich.

[73] Assignee: Warner-Lambert Company, Morris Plains, N.J.

[21] Appl. No.: 414,394

[22] Filed: Mar. 31, 1995

[51] Int. Cl.$^6$ .................. A61K 31/44; A61K 31/38; A61K 31/34; A61K 31/235; A61K 31/24; A61K 31/215; A61K 31/35

[52] U.S. Cl. .................. 514/332; 514/335; 514/444; 514/471; 514/472; 514/473; 514/461; 514/532; 514/538; 514/539; 514/530; 514/455; 514/437

[58] Field of Search .................. 514/532, 538, 514/539, 530, 455, 437, 332, 335, 444, 471, 472, 473, 461

[56] References Cited

U.S. PATENT DOCUMENTS

| | | | |
|---|---|---|---|
| 3,558,640 | 1/1971 | Shen et al. | 260/294.8 |
| 4,066,686 | 1/1978 | Lafon | 260/500.5 |
| 4,205,087 | 5/1980 | Waring | 424/317 |
| 4,489,095 | 12/1984 | Lafon | 424/315 |
| 4,964,893 | 10/1990 | Brannigan et al. | 71/88 |
| 5,366,982 | 11/1994 | Dereu et al. | 514/340 |

FOREIGN PATENT DOCUMENTS

| | | |
|---|---|---|
| 94/13635 | 6/1994 | WIPO . |
| 94/15932 | 7/1994 | WIPO . |
| 94/20480 | 9/1994 | WIPO . |

OTHER PUBLICATIONS

*Remingtons Pharmaceutical Sciences*, 16th Ed., 1980, p. 431.

*Primary Examiner*—Marianne M. Cintins
*Assistant Examiner*—William R. A. Jarvis
*Attorney, Agent, or Firm*—Todd M. Crissey

[57] ABSTRACT

The present invention provides a method of selectively inhibiting prostaglandin G/H synthase-2 that comprises administering to a patient in need of such inhibition an inhibiting amount of a compound having the Formula I, II or III

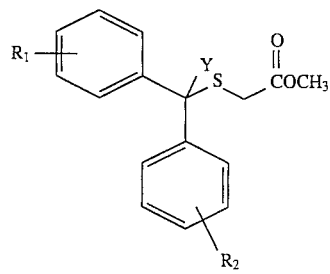

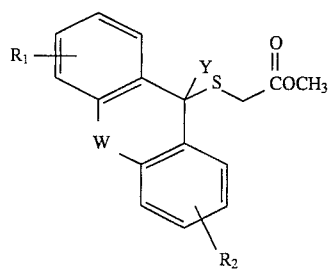

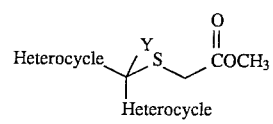

wherein the R groups and heterocycles are defined in the disclosure.

10 Claims, No Drawings

METHOD OF SELECTIVELY INHIBITING PROSTAGLANDIN G/H SYNTHASE-2

FIELD OF THE INVENTION

This invention relates to a method of selectively inhibiting prostaglandin G/H synthase-2. More particularly, this invention relates to a method of selectively inhibiting prostaglandin G/H synthase-2 comprising administering to a patient in need of such inhibition an inhibiting amount of a compound described herein.

BACKGROUND OF THE INVENTION

It is generally accepted by those skilled in the art that the pharmacology of nonsteroidal antiinflammatory drugs, also called NSAIDs, results from the inhibition of prostaglandin G/H synthase in arachidonic acid metabolism. Prostaglandin G/H synthase has also been called cyclooxygenase. Prostaglandin synthase activity results in the formation of prostaglandins and other arachidonic acid metabolites that are important inflammatory agents. These metabolites also have cytoprotective properties and are important for the maintenance of tissue physiology and homeostasis.

It has been recently discovered that there are two distinct isoforms of prostaglandin G/H synthase. The two forms have been called prostaglandin G/H synthase-1 and prostaglandin G/H synthase-2.

Prostaglandin G/H synthase-1 is a constitutive enzyme expressed in a variety of tissues and appears to be the isoform important for physiological and homeostatic processes. In contrast, prostaglandin G/H synthase-2 is upregulated by a variety of agents, including proinflammatorycytokines, endotoxins, mitogens, growth factors and hormones and is downregulated by glucocorticoids.

It is believed that prostaglandin G/H synthase-2 is responsible for the formation of prostaglandins and other arachidonic acid metabolites which contribute to the pathology of inflammation and other diseases.

In general, the nonsteroidal antiinflammatory drugs that are currently used to treat patients inhibit both prostaglandin G/H synthase-1 and prostaglandin G/H synthase-2, and therefore, have mechanism-based side effects due to the inhibition of prostaglandin G/H synthase-1 and the resulting interference with tissue homeostasis.

Compounds which inhibit prostaglandin G/H synthase-2, but have little or no effect on prostaglandin G/H synthase-1 can provide effective antiinflammatory, analgesic and antipyretic activity without causing side effects such as gastrointestinal and renal toxicities which are seen when using traditional nonsteroidal antiinflammatory drugs.

SUMMARY OF THE INVENTION

The present invention provides a method of selectively inhibiting prostaglandin G/H synthase-2 that comprises administering to a patient in need of such inhibition an inhibiting amount of a compound having the Formula I

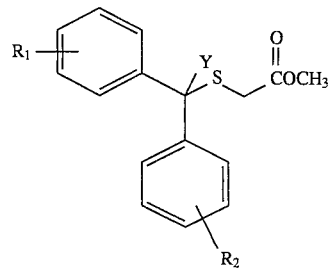

wherein $R_1$ and $R_2$ are independently hydrogen, halo, hydroxy, thiol, $C_1$–$C_6$ alkyl, $C_3$–$C_6$ cycloalkyl, $C_1$–$C_6$ alkoxy, phenyl, amino, dimethylamino or $S(O)_nR_3$, where $R_3$ is $C_1$–$C_6$ alkyl and n is 0, 1, or 2; and Y is hydrogen, phenyl or phenyl substitued with hydrogen, halo, hydroxy, thiol, $C_1$–$C_6$ alkyl, $C_3$–$C_6$ cycloalkyl, $C_1$–$C_6$ alkoxy, phenyl, amino, dimethylamino or $S(O)_nR_3$, where $R_3$ is $C_1$–$C_6$ alkyl and n is 0, 1, or 2;

or a compound having the Formula II

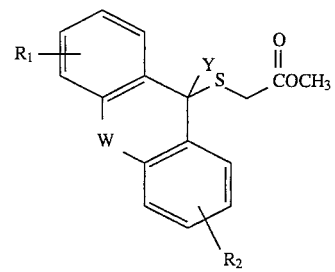

wherein $R_1$ and $R_2$ are independently hydrogen, halo, hydroxy, thiol, $C_1$–$C_6$ alkyl, $C_3$–$C_6$ cycloalkyl, $C_1$–$C_6$ alkoxy, phenyl, amino, dimethylamino or $S(O)_nR_3$, where $R_3$ is $C_1$–$C_6$ alkyl and n is 0, 1, or 2;

Y is hydrogen, phenyl or phenyl substitued with hydrogen, halo, hydroxy, thiol, $C_1$–$C_6$ alkyl, $C_3$–$C_6$ cycloalkyl, $C_1$–$C_6$ alkoxy, phenyl, amino, dimethylamino or $S(O)_nR_3$, where $R_3$ is $C_1$–$C_6$ alkyl and n is 0, 1, or 2; and W is a bond, O, S, CH=CH or $CH_2CH_2$;

or a compound having the Formula III

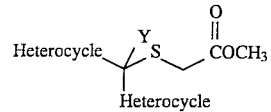

wherein the heterocycle is

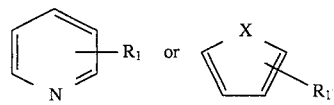

where X is O or S;

Y is hydrogen, phenyl or phenyl substitued with hydrogen, halo, hydroxy, thiol, $C_1$–$C_6$ alkyl, $C_3$–$C_6$ cycloalkyl, $C_1$–$C_6$ alkoxy, phenyl, amino, dimethylamino or $S(O)_nR_3$, where $R_3$ is $C_1$–$C_6$ alkyl and n is 0, 1, or 2; and $R_1$ is hydrogen, halo, hydroxy, thiol, $C_1$–$C_6$ alkyl, $C_3$–$C_6$ cycloalkyl, $C_1$–$C_6$ alkoxy, phenyl, amino, dimethylamino or $S(O)_nR_3$, where $R_3$ is $C_1$–$C_6$ alkyl and n is 0, 1, or 2.

DETAILED DESCRIPTION OF THE INVENTION

The present invention provides a method of selectively inhibiting prostaglandin G/H synthase-2, the method comprising administering to a patient in need of such inhibition an inhibiting amount of a compound having the Formula I

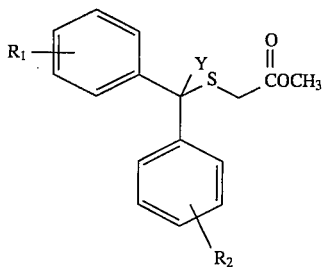

wherein $R_1$ and $R_2$ are independently hydrogen, halo, hydroxy, thiol, $C_1$–$C_6$ alkyl, $C_3$–$C_6$ cycloalkyl, $C_1$–$C_6$ alkoxy, phenyl, amino, dimethylamino or $S(O)_n R_3$, where $R_3$ is $C_1$–$C_6$ alkyl and n is 0, 1, or 2; and Y is hydrogen, phenyl or phenyl substitued with hydrogen, halo, hydroxy, thiol, $C_1$–$C_6$ alkyl, $C_3$–$C_6$ cycloalkyl, $C_1$–$C_6$ alkoxy, phenyl, amino, dimethylamino or $S(O)_n R_3$, where $R_3$ is $C_1$–$C_6$ alkyl and n is 0, 1, or 2;
or a compound having the Formula II

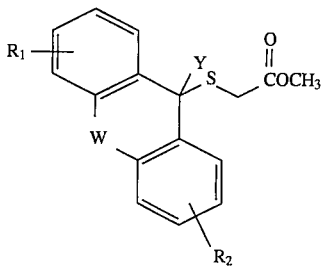

wherein $R_1$ and R2 are independently hydrogen, halo, hydroxy, thiol, $C_1$–$C_6$ alkyl, $C_3$–$C_6$ cycloalkyl, $C_1$–$C_6$ alkoxy, phenyl, amino, dimethylamino or $S(O)_n R_3$, where $R_3$ is $C_1$–$C_6$ alkyl and n is 0, 1, or 2;

Y is hydrogen, phenyl or phenyl substitued with hydrogen, halo, hydroxy, thiol, $C_1$–$C_6$ alkyl, $C_3$–$C_6$ cycloalkyl, $C_1$–$C_6$ alkoxy, phenyl, amino, dimethylamino or $S(O)_n R_3$, where $R_3$ is $C_1$–$C_6$ alkyl and n is 0, 1, or 2; and W is a bond, O, S, CH=CH or $CH_2CH_2$;
or a compound having the Formula III

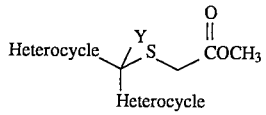

wherein the heterocycle is

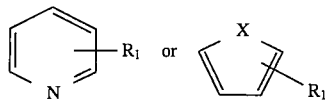

where X is O or S;
Y is hydrogen, phenyl or phenyl substitued with hydrogen, halo, hydroxy, thiol, $C_1$–$C_6$ alkyl, $C_3$–$C_6$ cycloalkyl, $C_1$–$C_6$ alkoxy, phenyl, amino, dimethylamino or $S(O)_n R_3$, where $R_3$ is $C_1$–$C_6$ alkyl and n is 0, 1, or 2; and $R_1$ is hydrogen, halo, hydroxy, thiol, $C_1$–$C_6$ alkyl, $C_3$–$C_6$ cycloalkyl, $C_1$–$C_6$ alkoxy, phenyl, amino, dimethylamino or $S(O)_n R_3$, where $R_3$ is $C_1$–$C_6$ alkyl and n is 0, 1, or 2.

The term "$C_1$–$C_6$ alkyl" means an alkyl radical, including a straight chain or branched radical, having from 1 to 6 carbon atoms. Representative examples of $C_1$–$C_6$ alkyl radicals include methyl, ethyl, n-propyl, isopropyl, n-butyl, isobutyl, tert-butyl, pentyl and hexyl.

The term "$C_3$–$C_6$ cycloalkyl" means an alkyl group that forms a ring structure. Representative examples of $C_3$–$C_6$ cycloalkyl radicals include cyclopropane, cyclobutane, cyclopentane and cyclohexane.

The term "$C_1$–$C_6$ alkoxy" means a $C_1$–$C_6$ alkyl radical bonded to an oxygen atom. Representative examples of $C_1$–$C_6$ alkoxy radicals include methoxy, ethoxy, propoxy, isopropoxy, n-butoxy, tert-butoxy, pentoxy and hexoxy.

The compounds of the present invention are administered to a patient. The term "patient" includes animals and humans. The patient to which the present compounds are administered have a condition that can be treated by inhibiting prostaglandin G/H synthase-2.

Compounds of the present invention are useful for the treatment of inflammation in a patient, and for treatment of other inflammation-associated disorders, for example, as an analgesic in the treatment of pain and headaches, or as an antipyretic for the treatment of fever. For example, compounds of the present invention are useful to treat arthritis, including but not limited to rheumatoid arthritis, spondyloarthopathies, gouty arthritis, systemic lupus erythematosus, osteoarthritis and juvenile arthritis. Compounds of the present invention are also useful in the treatment of asthma, bronchitis, menstrual cramps, tendinitis, bursitis, and skin related conditions such as psoriasis, eczema, burns and dermatitis, gastrointestinal conditions such as colon cancer, inflammatory bowel syndrome, Crohn's disease, gastritis, irritable bowel syndrome and ulcerative colitis, vascular diseases, migraine headaches, periarterisis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, hypersensitivity, conjunctivitis, gingivitis, swelling occurring after injury, myocardial ischemia, and the like.

The compounds of the present invention have a selectivity ratio of prostaglandin G/H synthase-2 to prostaglandin G/H synthase-1 in the range of about 2–1 to about 6–1. Preferably, the compounds of the present invention have a selectivity ratio in the range of about 4–1 to about 6–1. More preferably, the compounds have a selectivity ratio in the range of about 5–1 to about 6–1. The selectivities are determined using the procedure shown below in Example 19.

Those skilled in the art are familiar with the various conditions for which prostaglandin G/H synthase inhibitors can be used in a therapeutic regimen. Moreover, those skilled in the art are readily able to identify those patients in need of such inhibitors.

The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is sufficient. The specific dosage used, however, can vary. For example, the dosage can depended on a numbers of factors including the requirements of the patient, the severity of the condition being treated, and the pharmacological activity of the compound being used. The determination of optimum dosages for a particular patient is well known to those skilled in the art.

In one embodiment of the invention with respect to the compounds of Formula I, $R_1$ and $R_2$ are located at the ortho or para positions on the phenyl rings. In another embodiment, $R_1$ and $R_2$ are the same.

In another embodiment of the invention relating to the compounds of Formula I, $R_1$ and $R_2$ are hydrogen, methoxy, chlorine, dimethylamino, fluorine or methyl.

In yet another embodiment of the invention with respect to the compounds of Formula I, Y is phenyl.

With respect to the compounds of Formula II, $R_1$, $R_2$ and Y are preferably hydrogen. In another embodiment, W is a bond.

It is also contemplated that more than one compound of the present invention can be administered to a patient.

The compounds of the present invention can be administered to humans and animals either orally, rectally, parenterally (intravenously, intramuscularly or subcutaneously), intracisternally, intravaginally, intraperitoneally, intravesically, locally (powders, ointments or drops), or as buccal or nasal sprays.

The active component generally is present in about 5 to about 95% by weight of the entire composition. Preferably, the active component is present in about 30 to 70% by weight.

Compositions that contain a compound of the present invention that are suitable for parenteral injection may comprise physiologically acceptable sterile aqueous or non-aqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

The compositions may also contain adjuvants such as preserving, wetting, emulsifying and dispensing agents. Prevention of the action of microorganisms can be ensured by various antibacterial and antifungal agents, for example, parabens, chlorobutanol, phenol, sorbic acid and the like. It may also be desirable to include isotonic agents, for example sugars and sodium chloride and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the active compound is typically admixed with at least one inert excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alignates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example, paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols and the like.

Solid dosage forms such as tablets, dragees, capsules, pills and granules can be prepared with coatings and shells, such as enteric coatings and others well known in the art. They may contain opacifying agents and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the pharmacologically active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances and the like.

Besides such inert diluents, compositions containing the present compounds can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substance, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active compounds.

Dosage forms for topical administration of a compound of this invention include ointments, powders, sprays and inhalants. The active component is admixed under sterile conditions with a physiologically acceptable carrier and any preservatives, buffers or propellants as may be required. Ophthalamic formulations, eye ointments, powders and solutions are also contemplated as being within the scope of this invention.

The compounds of the present invention can exist in different stereoisometric forms by virtue of the presence of asymmetric centers in the compounds. It is contemplated that all stereoisometric forms of the compounds as well as mixture thereof, including racemic mixtures, form part of this invention.

In addition, the compounds of the present invention can exist in unsolvated as well as solvated forms with pharmaceutically acceptable solvents such as water, ethanol and the like. In general, the solvated forms are considered equivalent to the unsolvated forms for the purposes of the present invention.

In general, the compounds of the present invention can be prepared by the addition of methyl chloroacetate or methyl bromoacetate to a suitably substituted benzhydrylthiol in the presence of a base, preferably sodium hydride in a solvent such as tetrahydrofuran. Alternately, methyl thioglycolate is added to a benzhydryl halide in the presence of a base, preferably sodium hydride, in a solvent such as tetrahydrofuran. In those cases where a trityl or substituted trityl halide is used, the addition to methyl thioglycolate occurs in the absence of added base, when heated in a solvent such as toluene.

The compounds of the present invention can also be prepared by treatment of a suitably substituted benzhydrol with methyl thioglycolate. The preferred reaction conditions include the use of a catalytic amount of p-toluenesulfonic acid in toluene in the presence of activated molecular sieves. Alternatively, the suitably substituted benzhydrol and methyl thioglycolate are reacted in methanolic HCl.

In some situations, the compounds of the invention can be prepared via the corresponding carboxylic acid. Addition of thioglycolic acid to the suitable benzhydryl halide in toluene with a catalytic amount of p-toluenesulfonic acid in the presence of activated molecular sieves provides the intermediate acid. The acid is then esterified with diazomethane or preferably with acidic methanol to provide the compounds of the present invention.

The above-described reactions can also be used to prepare the compounds of the present invention that contain heterocyclic groups by starting with a heterocyclic compound that corresponds to the benzhydrylthio or benzhydryl halide.

Scheme 1 below shows various synthetic routes to the compounds used in the method of the present invention.

Scheme 1

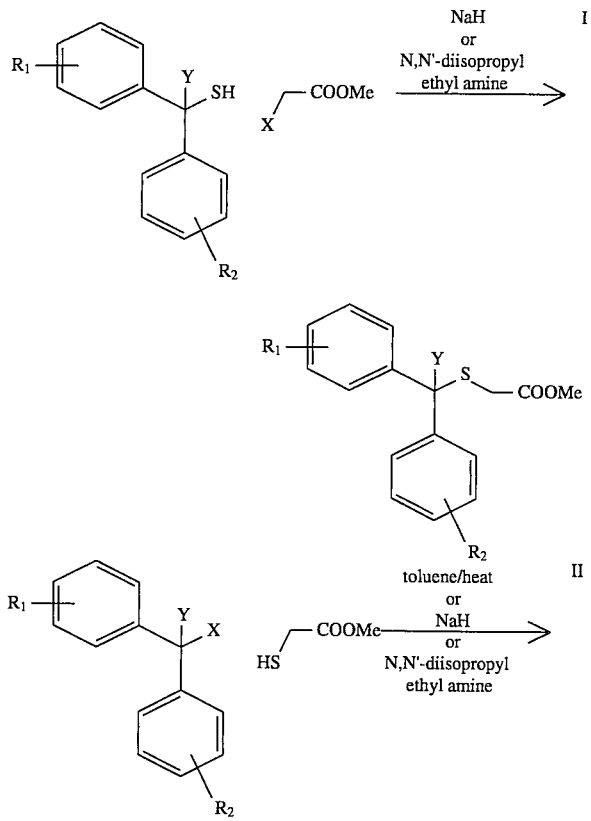

-continued
Scheme 1

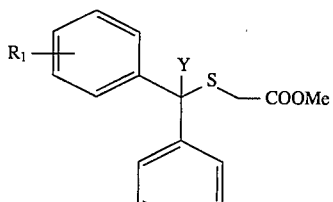

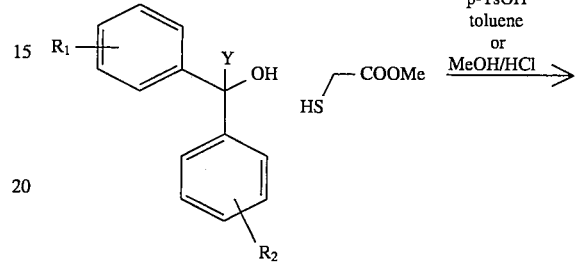

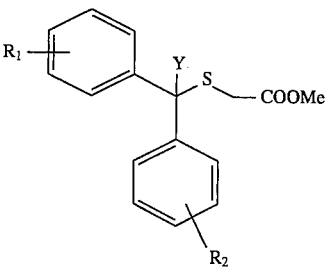

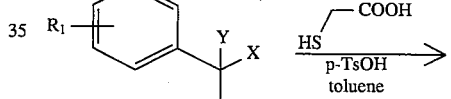

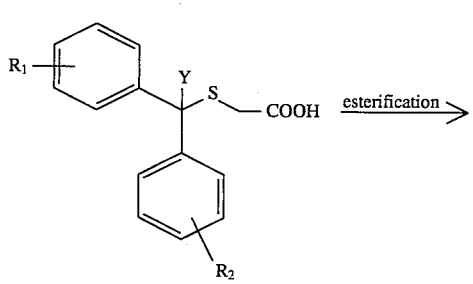

9
-continued
Scheme 1

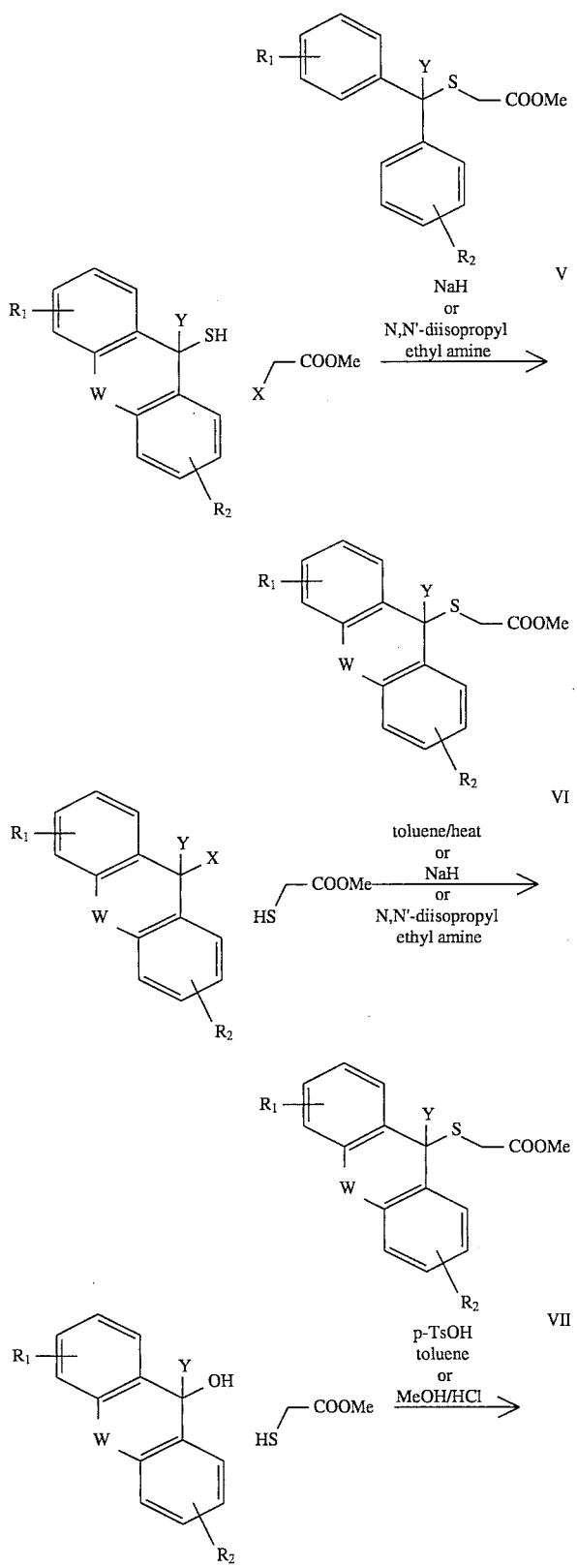

10
-continued
Scheme 1

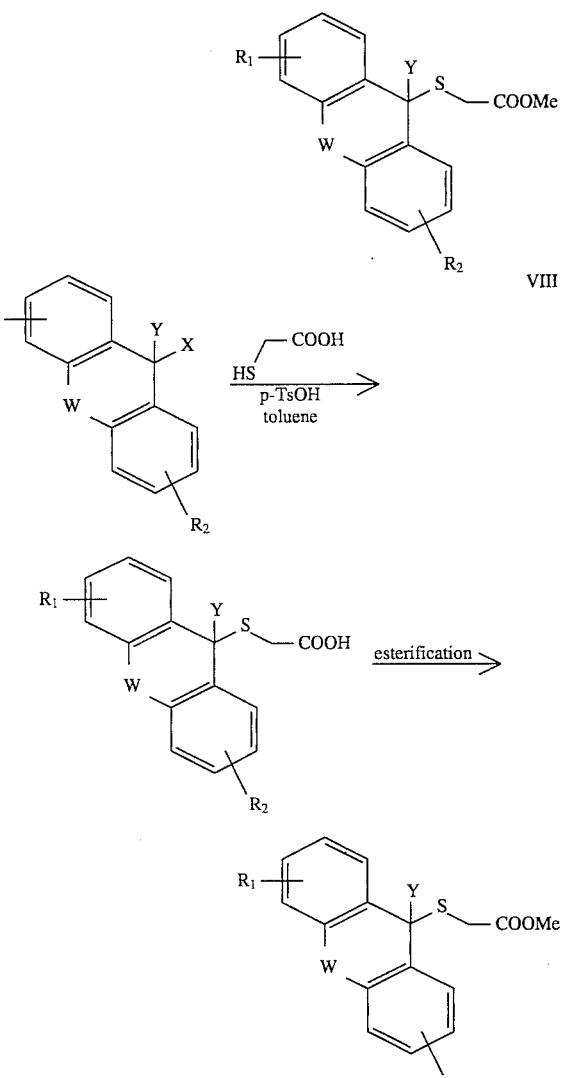

where $R_1$, $R_2$, Y and W are as defined above, X is halo, Me is methyl, MeOH is methanol and p-TsOH is p-toluenesulfonic acid.

The following examples illustrate particular embodiments of the invention and are not intended to limit the specification, including the claims, in any way.

EXAMPLES

Example 1

Methyl [(diphenylmethyl)thio]acetate

To a solution of methyl thioglycolate (5.95 g, 56 mmol) in 225 mL of tetrahydrofuran is added sodium hydride (2.5 g of 60% NaH in oil, 62.5 mmol). The mixture is stirred at room temperature for 10 minutes. Benzhydryl bromide (Aldrich of Milwaukee, Wis.; hereinafter "Aldrich") (15.3 g, 62 mmol) is added and the reaction mixture is stirred at room temperature for 3 days and then concentrated in vacuo. The residue is taken up in ethyl acetate and washed with saturated aqueous sodium bicarbonate, 10% aqueous citric acid, and brine and then dried over magnesium sulfate. Chromatography on silica gel, eluting with 4% ethyl acetate in hexane provides methyl [[(diphenyl)methyl]thio]acetate as a colorless oil in 15% yield.

Elemental Analysis: Calculated for $C_{16}H_{16}O_2S$: C, 70.56; H, 5.92;. Found: C, 70.11; H, 5.90.

Example 2

Methyl [[bis-(4-methoxyphenyl)methyl]thio]acetate

A solution of 4,4'-dimethoxybenzhydrol (Aldrich) (300 mg, 1.23 mmol) and methyl thioglycolate (123 mg, 1.35 mmol) in 6 mL of 10% methanolic HCl is heated at reflux for 45 minutes. The reaction is cooled to room temperature, diluted with ethyl acetate, washed with saturated aqueous sodium bicarbonate, brine and dried over magnesium sulfate. The product is concentrated in vacuo to give methyl [[bis-(4-methoxyphenyl)methyl]thio]acetate as a colorless oil in 73% yield.

Elemental Analysis: Calculated for $C_{18}H_{20}O_4S$: C, 65.04; H, 6.06; Found: C, 64.74; H, 6.05.

Example 3

Methyl [[bis-(4-chlorophenyl)methyl]thio]acetate

A solution of 4,4'-dichlorobenzhydrol (Aldrich) (500 mg, 1.97 mmol), mercaptoacetic acid (181 mg, 1.97 mmol) and p-toluenesulfonic acid monohydrate (93 mg, 0.49 mmol) in 7 mL of toluene is stirred at room temperature for 2 hours followed by heating at 50°–60° C. for 1 hour. Upon cooling, the mixture is diluted with ethyl acetate, washed with water, brine, and dried over magnesium sulfate. The product is concentrated in vacuo to give [[bis-(4-chlorophenyl)methyl]thio]acetic acid as a pale yellow oil.

The acid (646 mg, 1.98 mmol) is heated at reflux in 7 mL of 10% methanolic HCl for 45 minutes. The reaction is then cooled to room temperature, diluted with ethyl acetate, washed with saturated aqueous sodium bicarbonate, brine and dried over magnesium sulfate. Chromatography on silica gel, eluting with a gradient of 5% ethyl acetate in hexane to 10% ethyl acetate in hexane, provides methyl [[bis-(4-chlorophenyl)methyl]thio]acetate as a colorless oil in 56% yield.

Elemental Analysis:. Calculated for $C_{16}H_{14}Cl_2O_2S$: C, 56.31; H, 4.14; Found: C, 56.18; H, 4.10.

Example 4

Methyl [[bis-(4-dimethylaminophenyl)methyl]thio]acetate

A slurry of p-toluenesulfonic acid monohydrate (1.50 g, 7.89 mmol) and activated 3 Å molecular sieves (300–500 mg) in 7 mL of toluene is stirred for 15 minutes. Methyl thioglycolate (410 mg, 3.86 mmol) is then added followed by 4,4'-bis(dimethyamino)benzhydrol (Aldrich) (950 mg, 3.51 mmol) and stirred for 1 hour. The reaction is diluted with ethyl acetate, washed with saturated aqueous sodium bicarbonate, brine and dried over magnesium sulfate. Chromatography on silica gel, eluting with a 1:4 mixture of ethyl acetate: hexane, provides methyl [[bis-(4-dimethylaminophenyl)methyl]thio]acetate as a greenish yellow solid in 53% yield.

Elemental Analysis: Calculated for $C_{20}H_{26}N_2O_2S$: C, 67.01; H, 7.31; N, 7.81; Found: C, 66.69; H, 7.28; N, 7.73.

Example 5

Methyl [[bis-(4-fluorophenyl)methyl]thio]acetate

A slurry of p-toluenesulfonic acid monohydrate (108 mg, 0.57 mmol) and activated 3 Å molecular sieves (300–500 mg) in 4 mL of toluene is stirred for 15 minutes. Methyl thioglycolate (265 mg, 2.50 mmol ) is then added followed by 4,4'-difluoro-benzhydrol (Aldrich) (500 mg, 2.27 mmol). The reaction is stirred for 2.5 hours at room temperature followed by heating at 50°–60° C. for 45 minutes. The mixture is diluted with ethyl acetate, washed with saturated aqueous sodium bicarbonate, brine and dried over magnesium sulfate. Chromatography on silica gel, eluting with a gradient of 10% ethyl acetate in hexane to 20% ethyl acetate in hexane, provides methyl [[bis-(4-fluorophenyl)methyl]thio]acetate as a yellow oil in 50% yield.

Elemental Analysis: Calculated for $C_{16}H_{14}F_2O_2S$: C, 62.32; H, 4.58; Found: C, 62.50; H, 4.56.

Example 6

Methyl [[bis-(4-methylphenyl)methyl]thio]acetate

Following the procedure of Example 4, 4,4'-dimethylbenzhydrol, synthesized in accordance with M. R. Pavia, et. al. in *J. Med. Chem.* 35, 4238 (1992), is reacted with methyl thioglycolate for 18 hours at room temperature. Chromatography on silica gel, eluting with 10% ethyl acetate in hexane, gives methyl [[bis-(4-methylphenyl)methyl]thio]acetate as a colorless oil in 73% yield.

Elemental Analysis: Calculated for $C_{18}H_{20}O_2S$: C, 71.97; H, 6.71;. Found: C, 71.63; H, 6.63.

Example 7

Methyl [[bis-(2-chlorophenyl)methyl]thio]acetate

Following the procedure of Example 4, 2,2'-dichlorobenzhydrol, synthesized in accordance with C. W. N. Cumper, et. al. in *J. C. S. Perkins Trans. II* (1), 106 (1972)] is reacted with methyl thioglycolate for 4 hours at 50°–60° C. Chromatography on silica gel, eluting with a gradient of 5% ethyl acetate in hexane to 10% ethyl acetate in hexane, gives methyl [[bis-(2-chlorophenyl)methyl]thio]acetate as a white solid in 23% yield: melting point 90°–92° C.

Elemental Analysis: Calculated for $C_{16}H_{14}Cl_2O_2S$: C, 56.31; H, 4.14; Found: C, 56.19; H, 3.80.

Example 8

Methyl [[bis-(2-methoxyphenyl)methyl]thio]acetate

Following the procedure of Example 4, 2,2'-dimethoxybenzhydrol, synthesized in accordance with M. L. Hoefle, et. al. in *J. Med. Chem.* 34, 7 (1971)] is reacted with methyl thioglycolate for 3 hours at 50°–60° C. followed by 18 hours at room temperature. Chromatography on silica gel, eluting with a gradient of 10% ethyl acetate in hexane to 20% ethyl acetate in hexane, followed by additional chromatography, eluting with a gradient of 5% ethyl acetate in hexane to 10% ethyl acetate in hexane, gives methyl [[bis-(2-methoxyphenyl)methyl]thio]acetate as a white solid in 72% yield: melting point 65°–67° C.

Elemental Analysis: Calculated for $C_{18}H_{20}O_4S$: C, 65.04; H, 6.06; Found: C, 64.49; H, 6.13.

Example 9

Methyl [[bis-(2-thienyl)methyl]thio]acetate

To a −35° to −40° C. solution of 2-(then-2-oyl)thiophene (Maybridge of Cornwall, UK) (500 mg, 2.60 mmol) in 10 mL of methylene chloride, is added dropwise a 1M solution of diisobutylaluminum hydride in methylene chloride (6.50 mL, 6.50 mmol) over 20 minutes. The reaction is stirred at −40° C. for 2.5 hours and then quenched by the slow addition of 10 mL of methanol. The mixture is warmed to room temperature and poured into 100 mL of saturated aqueous sodium tartrate. The aqueous solution is extracted with several portions of methylene chloride, the organic extracts combined, and dried over magnesium sulfate. Chromatography on silica gel, eluting with a 1:2 mixture of ethyl acetate to hexane, gives di-2-thienylmethanol as a light orange solid in 54% yield.

A slurry of ρ-toluenesulfonic acid monohydrate (47 mg, 0.25 mmol) and activated 3 Å molecular sieves (300–500 mg) in 5 mL of toluene is stirred for 15 minutes. Methyl thioglycolate (108 mg, 1.02 mmol) is added followed by di-2-thienylmethanol (200 mg, 1.02 mmol) and the mixture is stirred for 4 hours at room temperature. The reaction is diluted with ethyl acetate, washed with saturated aqueous sodium bicarbonate, brine and dried over magnesium sulfate. Chromatography on silica gel, eluting with a 1:4 mixture of ethyl acetate: hexane gives methyl [[bis-(napth-2-yl)methyl]thio]acetate as an orange oil in 57% yield.

Elemental Analysis: Calculated for $C_{12}H_{12}O_2S_3$: C, 50.68; H, 4.25; Found: C, 50.84; H, 4.31.

Example 10

Methyl (9-fluorenylthio)acetate

To a suspension of sodium hydride (840 mg of 60% NaH in oil, 21.0 mmol) in 40 mL of tetrahydrofuran is added methyl thioglycolate (1.68 mL, 18.8 mmol). The mixture is stirred at room temperature for 20 minutes. 9-Bromofluorene (Aldrich) (5.23 g, 21.3 mmol) in 30 mL of tetrahydrofuran is added and the reaction mixture is stirred at room temperature overnight then concentrated to dryness. The residue is taken up in ethyl acetate and washed with brine, saturated aqueous sodium bicarbonate, and again with brine. The organic layer is dried over magnesium sulfate, concentrated in vacuo and chromatographed on silica gel, eluting with 10% ethyl acetate in hexane to provide 908 mg (18%) of methyl (9-fluorenylthio)acetate as a colorless oil.

Elemental Analysis: Calculated for $C_{16}H_{14}O_2S$: C, 71.08; H, 5.22;. Found: C, 71.31; H, 5.40.

Example 11

Methyl [(triphenylmethyl)thio]acetate

A solution of trityl chloride (Aldrich) (5.0 g, 17.9 mmol) and methyl thioglycolate (2.1 mL, 23.3 mmol) in 50 mL of toluene is heated at reflux overnight. The reaction solution is cooled and concentrated in vacuo. The oily residue is crystallized from ethyl acetate/hexane to give 5.4 g (87%) of methyl [(triphenylmethyl)thio]acetate: melting point 111°–115° C.

Elemental Analysis: Calculated for $C_{22}H_{20}O_2S$: C, 75.83; H, 5.7; Found: C, 75.47; H, 5.91.

Example 12

Methyl [[(tris-4-methoxyphenyl)methyl]thio]acetate

A solution of 4, 4', 4"-trimethoxytrityl chloride (Aldrich) (2.2 g, 6.0 mmol) and methyl thioglycolate (0.70 mL, 7.8 mmol) in 25 mL of toluene is heated at reflux for 4 hours. The reaction is cooled and concentrated in vacuo. The oily residue is chromatographed on silica gel eluting with a gradient of ethyl acetate:toluene:hexane (3:27:70 to 5:40:55). The purified product is co-evaporated with hexane 3 times resulting in a gummy semi-solid, that is stirred in a mixture of ethyl acetate:hexane (5:95) for 3 days. The resultant solid is collected by filtration to give 0.8 g (31%) of methyl [[(tris-4-methoxyphenyl)methyl]thio]acetate: melting point 90°–93° C.

Elemental Analysis: Calculated for $C_{25}H_{26}O_5S$: C, 68.47; H, 5.98; Found: C, 68.07; H, 5.93.

Example 13

Methyl [[(bis-4-methoxyphenyl)phenylmethyl]thio]acetate

A solution of 4,4'-dimethoxytrityl chloride (Aldrich) (2.0 g, 6.0 mmol) and methyl thioglycolate (0.70 mL, 7.8 mmol) in 50 mL of toluene is heated at reflux for 4 hours. The reaction is cooled and diluted with ethyl acetate. The solution is washed with 1N HCl, water, a saturated aqueous sodium bicarbonate, and then brine. The organic phase is dried over magnesium sulfate, filtered, and concentrated in vacuo. The resulting oil is chromatographed on silica gel eluting with a gradient of ethyl acetate:toluene:hexane (3:27:70 to 5:25:70) to give 2.0 g (80%) of methyl [[(bis-4-methoxyphenyl)phenylmethyl]thio]acetate: melting point 108°–110° C.

Elemental Analysis: Calculated for $C_{24}H_{24}O_4S$: C, 70.56; H, 5.92; Found: C, 70.36; H, 6.04.

Example 14

Methyl (9-phenylfluoren-9-yl-thio)acetate

A solution of 9-bromo-9-phenylfluorene (Aldrich) (1.9 g, 5.9 mmol) and methyl thioglycolate (0.70 mL, 7.8 mmol) in 50 mL of toluene is heated at reflux for 4 hours. The reaction is cooled and concentrated in vacuo. The resulting oil is chromatographed on silica gel eluting with a gradient of ethyl acetate/toluene/hexane (3:20:77 to 5:40:55). The purified product is co-evaporated with hexane 2 times and dried under vacuum for 3 days to give 1.6 g (77%) of methyl (9-phenylfluoren-9-yl-thio)acetate as an oil.

Elemental Analysis: Calculated for $C_{22}H_{18}O_2S$: C, 76.27; H, 5.24; Found: C, 76.06; H, 5.21.

Example 15

Methyl (5H-dibenzo[a,d]cyclohepten-5-yl-thio)acetate

Acetyl chloride (171 μL, 2.4 mmol) is carefully added to 8 mL of dry methanol and the solution is stirred for 15 minutes. Methyl thioglycolate (257 μL, 2.9mmol) and dibenzosuberenol (Aldrich) (0.50 g, 2.4 mmol) are added, and the reaction is stirred for 5 minutes. The reaction is diluted with ethyl acetate and washed with saturated aqueous sodium bicarbonate, water, then brine. The organic phase is dried over magnesium sulfate, filtered, and concentrated in vacuo. The resulting oil is chromatographed on silica gel eluting with ethyl acetate:toluene:hexane (3:27:70) to give 0.62 g (87%) of methyl (5H-dibenzo[a,d]cyclohepten-5-yl-thio)acetate: melting point 74°–76° C.

Elemental Analysis: Calculated for $C_{18}H_{16}O_2S$: C, 72.94; H, 5.44; Found: C, 72.80; H, 5.52.

Example 16

Methyl (xanthen-9-yl-thio)acetate

A solution of 9-hydroxyxanthene (Aldrich) (1.0 g, 5.0 mmol), thioglycolic acid (42 µL, 6.0 mmol), and p-toluenesulfonic acid monohydrate (10 mg) in 10 mL of toluene is stirred for 30 minutes. The reaction is diluted with ethyl acetate and washed 3 times with water and once with brine. The organic phase is dried over magnesium sulfate, filtered and concentrated in vacuo. The resulting solid is chromatographed twice on silica gel eluting with methanol:chloroform (5:95) to give 1.0 g (72%) of xanthen- 9-yl-thioacetic acid: melting point 131°–132° C.

Acetyl chloride (196 µL, 2.75 mmol) is carefully added to 9 mL of dry methanol and stirred for 15 minutes. Xanthen-9-yl-thioacetic acid (250 mg, 0.92 mmol) is added, and the reaction is stirred for 1.5 hours. The reaction solution is diluted with ethyl acetate and washed twice with saturated aqueous sodium bicarbonate, once with water, followed by brine. The organic phase is dried over magnesium sulfate, filtered, and concentrated in vacuo giving 245 mg (93%) of methyl (xanthen-9-yl-thio)acetate as an oil.

Elemental Analysis: Calculated for $C_{16}H_{14}O_3S$: C, 67.11; H, 4.93; Found: C, 66.86; H, 5.03.

Example 17

Methyl (10, 11-dihydro-5H-dibenzo[a,d]cyclohepten-5-yl-thio)acetate

N,N-diisopropylethylamine (590 µL, 3.3 mmol) is added to a solution of 5-chlorodibenzosuberane (Aldrich) (0.50 g, 2.2 mmol) and methyl thioglycolate (230 µL, 2.6 mmol) in 2.7 mL of dimethylformamide, and the reaction is stirred for 1 hour. The reaction solution is diluted with ethyl acetate and washed twice with 1N HCl, followed by water, saturated aqueous sodium bicarbonate and brine. The organic phase is dried over magnesium sulfate, filtered and concentrated in vacuo. The resulting oil is chromatographed on silica gel eluting with ethyl acetate:toluene:hexane (2:18:80) to give 0.49 g (75%) of methyl (10, 11-dihydro- 5H-dibenzo[a,d]cyclohepten-5-yl-thio) acetate: melting point 68°–69° C.

Elemental Analysis: Calculated for $C_{18}H_{18}O_2S$: C, 72.45; H, 6.08; Found: C, 72.26; H, 6.22.

Example 18

Methyl [[(4-methylthiophenyl)phenylmethyl]thio]acetate

A solution of 4-bromophenyl methyl sulfide (Aldrich) (3.3 g, 16.4 mmol) in 10 mL of dry diethyl ether is slowly added to a stirred suspension of magnesium turnings (0.44 g, 18.1 mmol) and three crystals of iodine in 10 mL of boiling dry diethyl ether. The reaction is heated at reflux for several hours until almost all the magnesium is consumed. The reaction is cooled to room temperature, and a solution of benzaldehyde (2.0 mL, 19.7 mmol) in 50 mL of dry diethyl ether is added dropwise. The reaction mixture is diluted with ethyl acetate and washed twice with 1N HCl, followed by saturated aqueous sodium bicarbonate, and brine. The organic phase is dried over magnesium sulfate, filtered, and concentrated in vacuo. The resulting crude solid is crystallized from diethyl ether/hexane to give 2.4 g (64%) of 4-methylthiobenzhydrol: melting point 92°–93.5° C.

Elemental Analysis: Calculated for $C_{14}H_{14}OS$: C, 73.01; H, 6.13; Found: C, 72.93; H, 6.05.

To a solution of p-toluenesulfonic acid monohydrate (50 mg, 0.3 mmol) in 10 mL of toluene, which contains 300–500 mg of activated 3 Å molecular sieves, is added 4-methylthiobenzhydrol (0.30 g, 1.3 mmol) and methyl thioglycolate (140 µL, 1.6 mmol), and the reaction is stirred for 2 hours. The reaction is diluted with ethyl acetate and washed with a saturated solution of sodium bicarbonate, water, followed by brine. The organic phase is dried over magnesium sulfate, filtered, and concentrated in vacuo. The resulting oil is chromatographed on silica gel eluting with ethyl acetate::toluene:hexane (2:18:80) to give 0.23 g (56%) of methyl [[(4-methylthiophenyl)phenylmethyl]thio]acetate as an oil.

Elemental Analysis: Calculated for $C_{17}H_{18}O_2S_2$: C, 64.12; H, 5.70. Found: C, 64.13; H, 5.67.

Example 19

Inhibition Studies

The compounds of the present invention were evaluated as selective inhibitors of prostaglandin G/H synthase-2 by determining the effect of the compounds on the conversion of [$^{14}C$]arachidonic acid to products by prostaglandin G/H synthase-2 purified from sheep placenta. This enzyme shares immunoreactivity and sequence homology with human prostaglandin G/H synthase-2. The effects of the compounds on prostaglandin G/H synthase-1 purified from ram seminal vesicles is used for the evaluation of inhibitory selectivity.

Each compound was preincubated for 15 minutes at room temperature in 50 mM sodium phosphate buffer at pH 7.4 containing 3.33 mM reduced glutathione, 2.67 mM epinephrine and 6.6% dimethylsulfoxide with sufficient enzyme to cause approximately 30% conversion of substrate to products after 15 minutes incubation in the absence of inhibitory compounds. Reactions with 24 µM arachidonic acid are initiated by the addition of a one third volume of 50 mM sodium phosphate buffer, pH 7.4, containing 3.33 mM reduced glutathione, 2.67 mM epinephrineβ and [$^{14}C$] arachidonic acid.

Reactions were terminated after 15 minutes incubation at room temperature by the addition of 1.875 volumes of methanol:acetic acid (100:0.1) containing 0.5 mg/ml triphenylphosphine. The reaction products were separated from the unconverted substrate by high performance liquid chromatography and quantified by on-line radiometric detection. Compound effects were computed as percent inhibition of blank-adjusted mean product formation in uninhibited incubations. The results of these tests are shown below in Table 1.

TABLE 1

| Example No. | % Inhibition of PGHS-2 at 100 µM | % Inhibition of PGHS-2 at 10 µM | % Inhibition of PGHS-1 at 100 µM | % Inhibition of PGHS-1 at 10 µM |
| --- | --- | --- | --- | --- |
| 1 | 84 | 56 | 42 | 20 |
| 2 | 79 | 23 | <10 | <10 |
|  | 74 | 34 | 13 | <10 |

TABLE 1-continued

| Example No. | % Inhibition of PGHS-2 at 100 μM | % Inhibition of PGHS-2 at 10 μM | % Inhibition of PGHS-1 at 100 μM | % Inhibition of PGHS-1 at 10 μM |
| --- | --- | --- | --- | --- |
| 3 | 45 | <10 | <10 | <10 |
|   | 46 | 26 | 70 | 41 |
| 4 | 96 | 86 | 68 | 42 |
|   | 99 | 92 | 72 | 31 |
|   | 92 | 86 |   |   |
| 5 | 52 | <10 | <10 | <10 |
|   | 40 | 41 |   |   |
| 6 | 52 | 11 | <10 | <10 |
| 7 | 37 | <10 | <10 | <10 |
| 8 | 77 | 14 | Not run | Not run |
| 9 | 33 | <10 | <10 | <10 |
| 10 | 77 | 30 | 18 | <10 |
| 11 | 62 | 29 | 10 | <10 |
| 12 | 80 | 79 | 32 | 32 |
|   | 86 | 83 | 17 | 13 |
| 13 | 49 | 41 | <10 | <10 |
| 14 | 50 | 14 | <10 | <10 |
| 15 | 31 | <10 | <10 | <10 |
| 16 | 78 | 41 | 13 | <10 |
|   | 85 | 50 | 34 | <10 |
| 17 | 17 | 8 | <10 | <10 |

PGHS-2 is prostaglandin G/H synthase-2 and PGHS-1 is prostaglandin synthase-1.

What is claimed is:

1. A method of selectively inhibiting prostaglandin G/H synthase-2, the method comprising administering to a patient in need of such inhibition an inhibiting amount of a compound having the Formula I

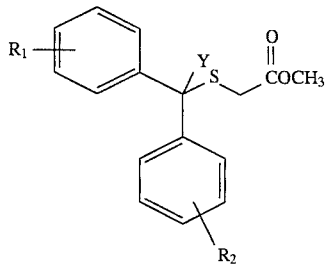

wherein $R_1$ and $R_2$ are independently hydrogen, halo, hydroxy, thiol, $C_1$–$C_6$ alkyl, $C_3$–$C_6$ cycloalkyl, $C_1$–$C_6$ alkoxy, phenyl, amino, dimethylamino or $S(O)_nR_3$, where $R_3$ is $C_1$–$C_6$ alkyl and n is 0, 1, or 2; and Y is hydrogen, phenyl or phenyl substitued with hydrogen, halo, hydroxy, thiol, $C_1$–$C_6$ alkyl, $C_3$–$C_6$ cycloalkyl, $C_1$–$C_6$ alkoxy, phenyl, amino, dimethylamino or $S(O)_nR_3$, where $R_3$ is $C_1$–$C_6$ alkyl and n is 0, 1, or 2.

2. The method of claim 1 wherein $R_1$ and $R_2$ are located at the para positions of the phenyl rings.

3. The method of claim 1 wherein $R_1$ and $R_2$ are the same.

4. The method of claim 1 wherein $R_1$ and $R_2$ are located at the ortho positions of the phenyl rings.

5. The method of claim 3 wherein $R_1$ and $R_2$ are hydrogen, methoxy, chlorine, dimethylamino, fluorine or methyl.

6. The method of claim 1 wherein Y is phenyl.

7. A method of selectively inhibiting prostaglandin G/H synthase-2, the method comprising administering to a patient in need of such inhibition an inhibiting amount of a compound having the Formula II

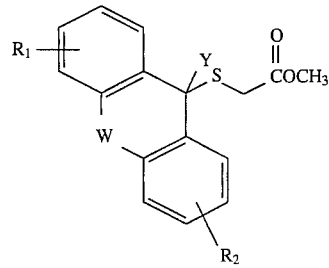

wherein $R_1$ and $R_2$ are independently hydrogen, halo, hydroxy, thiol, $C_1$–$C_6$ alkyl, $C_3$–$C_6$ cycloalkyl, $C_1$–$C_6$ alkoxy, phenyl, amino, dimethylamino or $S(O)_nR_3$, where $R_3$ is $C_1$–$C_6$ alkyl and n is 0, 1, or 2;

Y is hydrogen, phenyl or phenyl substitued with hydrogen, halo, hydroxy, thiol, $C_1$–$C_6$ alkyl, $C_3$–$C_6$ cycloalkyl, $C_1$–$C_6$ alkoxy, phenyl, amino, dimethylamino or $S(O)_nR_3$, where $R_3$ is $C_1$–$C_6$ alkyl and n is 0, 1, or 2; and W is a bond, O, S, CH=CH or $CH_2CH_2$.

8. The method of claim 7 wherein $R_1$, $R_2$ and Y are hydrogen.

9. The method of claim 7 wherein W is a bond.

10. A method of selectively inhibiting prostaglandin G/H synthase-2, the method comprising administering to a patient in need of such inhibition an inhibiting amount of a compound having the Formula III

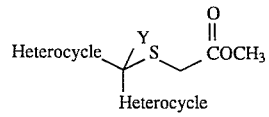

wherein the heterocycle is

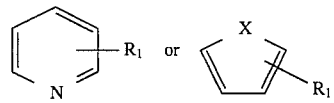

where X is O or S;

Y is hydrogen, phenyl or phenyl substitued with hydrogen, halo, hydroxy, thiol, $C_1$–$C_6$ alkyl, $C_3$–$C_6$ cycloalkyl, $C_1$–$C_6$ alkoxy, phenyl, amino, dimethylamino or $S(O)_nR_3$, where $R_3$ is $C_1$–$C_6$ alkyl and n is 0, 1, or 2; and $R_1$ is hydrogen, halo, hydroxy, thiol, $C_1$–$C_6$ alkyl, $C_3$–$C_6$ cycloalkyl, $C_1$–$C_6$ alkoxy, phenyl, amino, dimethylamino or $S(O)_nR_3$, where $R_3$ is $C_1$–$C_6$ alkyl and n is 0, 1, or 2.

* * * * *